US006267730B1

(12) United States Patent
Pacunas

(10) Patent No.: US 6,267,730 B1
(45) Date of Patent: Jul. 31, 2001

(54) APNEA DETECTING SYSTEM

(76) Inventor: Kenneth M. Pacunas, 4 Miltimore Rd., Derry, NH (US) 03038

( * ) Notice: Subject to any disclaimer, the term of this patent is extended or adjusted under 35 U.S.C. 154(b) by 0 days.

(21) Appl. No.: 09/379,977

(22) Filed: Aug. 24, 1999

Related U.S. Application Data

(60) Provisional application No. 60/097,815, filed on Aug. 25, 1998, and provisional application No. 60/117,935, filed on Jan. 29, 1999.

(51) Int. Cl.[7] ..... A61B 5/08

(52) U.S. Cl. ..... 600/534; 600/529

(58) Field of Search ..... 600/534, 535, 600/536, 533, 529, 587

(56) References Cited

U.S. PATENT DOCUMENTS 3,782,368 * 1/1974 Reibold ..... 600/534
4,696,307 9/1987 Montigieux .
4,989,612 * 2/1991 Fore ..... 600/534
5,099,702 3/1992 French .
5,107,855 * 4/1992 Harrington et al. ..... 600/534
5,277,194 1/1994 Hosterman et al. .
5,295,490 * 3/1994 Dodakian ..... 600/534
5,400,012 3/1995 Walton .
5,454,376 * 10/1995 Stephens et al. ..... 600/534
5,615,688 * 4/1997 O'Dwyer ..... 600/534
5,864,291 * 1/1999 Walton ..... 600/534
5,928,157 * 7/1999 O'Dwyer ..... 600/534

* cited by examiner

*Primary Examiner*—Eric F. Winakur
*Assistant Examiner*—Navin Natnithithadha
(74) *Attorney, Agent, or Firm*—O'Connell Law Firm

(57) ABSTRACT

An apnea detecting system for monitoring a cyclic respiratory movement of a subject's body and for triggering an alarm signal in response to an abnormality in that respiratory movement. The apnea detecting system includes a specially designed article of clothing, which may comprise a diaper, for retaining an apnea detector adjacent to a subject's body. A projection from a body of the apnea detector cooperates with a plunger actuator and a piezoelectric member to sense a respiratory movement of a subject. The article of clothing has a body-covering element with an aperture therein for aligning with the projection on the apnea detector. The apnea detector is retained relative to the article of clothing with the projection aligned with the aperture by a pocket. First and second legs may project from the apnea detector body to be received through a slit in an outside wall of the pocket for securing the apnea detector within the pocket. A speaker disposed on the first leg may provide an alarm signal in the event of a detected abnormality in the subject's respiratory movement.

33 Claims, 8 Drawing Sheets

10 3 46 14 12 11 17 19 54 60 58 16 56 3

APNEA DETECTING SYSTEM

This appln is claims the benefit of Provisional Nos. 60/097,815 filed Aug. 25, 1998 and 60/117,935 filed Jan. 29, 1999.

FIELD OF THE INVENTION

The present invention relates to an apnea detecting system for monitoring the cyclic respiratory movement of a subject's body and for triggering an alarm signal in response to a cessation in that respiratory movement.

BACKGROUND OF THE INVENTION

Sudden infant death syndrome, commonly referred to by its acronym of SIDS, remains a mysterious phenomenon that can be an overwhelming source of anxiety to parents of newborns. Although the precise source of SIDS continues to elude researchers, it is indisputably true that an occurrence of SIDS will be attended by a cessation in breathing, which is commonly termed apnea. Accordingly, anxious parents often find themselves physically watching over their sleeping babies or listening to baby monitors in the hope of detecting any breathing affectation and preventing that apnea occurrence from leading to a life threatening event.

One knowledgeable in the art will be aware that a plurality of inventors have endeavored to provide means for continuously monitoring an infant's breathing and for triggering an alarm signal in response to a cessation in that breathing. The prior art has disclosed apnea detectors with a wide variety of means for detecting a cessation in breathing. Almost universally, these apnea detectors have been retained adjacent to a child's body by a strap that surrounds the child's torso. Certain of these devices further require that adhesive be interposed between the child's body and a housing of the apnea detector for ensuring constant contact and proper function of the device.

Unfortunately, the apnea detectors disclosed by the prior art suffer from a number of drawbacks. A most basic disadvantage of prior art apnea detectors is that securing the device about a child's torso is a relatively cumbersome task that certainly makes applying the device an unduly laborious that could discourage the apnea detector from being applied at all. Furthermore, strapping such apnea detectors around a baby's waist certainly can lead to discomfort for the child, which can be upsetting both to the child and to the parent. Still further, many prior art apnea detectors require a measure of expertise and a considerable degree of care to ensure that the device is installed properly on a wearer.

Even further still, the retaining straps in prior art devices can become displaced, which can prevent the devices from functioning properly and could pose a danger of entanglement or strangulation to the young, sleeping wearer. This same danger is often unfortunately presented by apnea detectors that employ external wires or leads for their sensing functions, power supply, or the like. Yet further, AC powered apnea detectors could exhibit EMF generation, which also would endanger the subject whom they are intended to protect. On a more mundane level, one will appreciate that many prior art apnea detectors are necessarily expensive to manufacture and thus to buy, which can put them out of reach of many consumers.

In light of the foregoing, it becomes clear that an apnea detector providing a solution to one or more of the aforementioned deficiencies in the prior art would be useful. It is clearer still that an apnea detector presenting a solution to each and every problem left by the prior art while providing a number of heretofore unrealized advantages would represent a marked advance in the art.

SUMMARY OF THE INVENTION

Advantageously, the present invention sets about with the broadly stated object of providing an apnea detecting system that meets the needs left unmet by the prior art while markedly improving on the functionality of the prior art. Naturally, a primary object of the present invention is that of providing a device that consistently functions effectively to ensure that any cessation or other appreciable affectation in a wearer's breathing will be detected and an alarm signal actuated in response thereto. In furtherance of this basic object, a principal object of the present invention is to provide an apnea detector that is retained securely in place while remaining comfortably unobtrusive. Another object of the invention is to provide an apnea detector that effectively can not act as an independent source of danger to a child who wears the device. A still further object of the invention is to provide an apnea detector that may be installed quickly and easily in a manner that requires substantially no expertise and leaves little room for error. Yet another object of the invention is to provide an apnea detector that is durable and reliable in function yet inexpensive in manufacture. Certainly these and further objects and advantages of the present invention will be obvious both to one who reviews the present disclosure and to one who has an opportunity to make use of an embodiment of the present invention.

In accomplishing the aforementioned objects, one most basically stated embodiment of the present invention for an apnea detecting system essentially comprises an apnea detector for monitoring a cyclic respiratory movement of a subject's body and for triggering an alarm signal in response to an abnormality in that respiratory movement in combination with an article of clothing specifically adapted for retaining the apnea detector.

A resilient projection may be disposed on the first side of the body of the apnea detector. The resilient projection preferably will be formed integrally as a single member with a wall of the apnea detector body. The resilient projection may be formed as a hub coupled to the wall by a plurality of legs. The resilient projection may cooperate with a plunger actuator and a piezoelectric member to act as a means for sensing a respiratory movement of a subject. In such a case, the plunger actuator may have a first end coupled to an interior surface of the resilient projection and a second end disposed adjacent to the piezoelectric member for deforming the piezoelectric member upon compression of the resilient projection. The sensing means may be supplemented by a means for triggering an alarm signal in response to an abnormality in the respiratory movement of a subject and a means for providing an alarm signal in response to an activation by the alarm signal triggering means.

The article of clothing, which may assume the form of a diaper, most basically comprises a body covering element with an aperture, which may be annular, therein for aligning with the projection from the body of an apnea detector. The article of clothing further includes a means for retaining the apnea detector relative to the article of clothing with the resilient projection aligned with the aperture in the article of clothing. With the means for retaining the apnea detector relative to the article of clothing, the invention ensures consistently effective function of the apnea detector.

The means for retaining the apnea detector relative to the article of clothing may comprise a pocket disposed on the body covering element, and the aperture may be disposed on an inside wall of the pocket. The article of clothing may include another aperture, such as a slit, in the outside wall of the pocket. A first leg may project from the second side of the apnea detector for engaging the aperture in the outside wall of the pocket. With this, the aperture and the first leg together act as an ideal means for securing the apnea detector within the pocket.

The first leg preferably will be supplemented by a second leg so that the apnea detector will be retained within the pocket most securely. The first and second legs may be fixed in position with a proximal side of each leg facing the body of the apnea detector and a distal side of each leg facing away from the body of the apnea detector. Alternatively, the legs could be hingedly coupled to the apnea detector body and locked in the aforedescribed configuration by a means for locking the first and second legs in position, which may comprise a hook in combination with a ridge. A most effective alarm indication may be provided by disposing a means for providing an alarm signal, such as a speaker, on the distal side of the first leg so that the speaker or the like will be disposed exterior to the outside wall of the pocket when the apnea detector is disposed within the pocket.

An alternative apnea detecting system may be constructed with the apnea detector body comprising a first section and a second section. The first section may be coupled to the second section by a hinge member. In such an embodiment, the means for sensing a respiratory movement of a subject may comprise a piezoelectric member coupled at a first location to the first section of the apnea detector body and coupled at a second location to the second section of the apnea detector body. The piezoelectric member thus will act as a bridge between the first and second sections of the apnea detector body. Consequently, a pivoting of the first section relative to the second section will tend to cause mechanical strain in the piezoelectric member. This mechanical strain will then provide a signal indicative of respiratory movement. With this, one sees that the piezoelectric member acts as a means for converting a mechanical movement of the first section relative to the second section to an electrical signal.

Of course, one should remain mindful that the foregoing discussion is designed merely to outline broadly the more important features of the invention to enable a better understanding of the detailed description that follows and to instill a better appreciation of the inventor's contribution to the art. Before an embodiment of the invention is explained in detail, it must be made clear that the following details of construction, descriptions of geometry, and illustrations of inventive concepts are mere examples of possible manifestations of the invention.

DETAILED DESCRIPTION OF PREFERRED EMBODIMENTS

To assist one in better understanding and, in appropriate circumstances, practicing the present invention, certain preferred embodiments of the instant invention for an apnea detector are shown in the accompanying figures, which will be described with particularity below.

Figure 1:
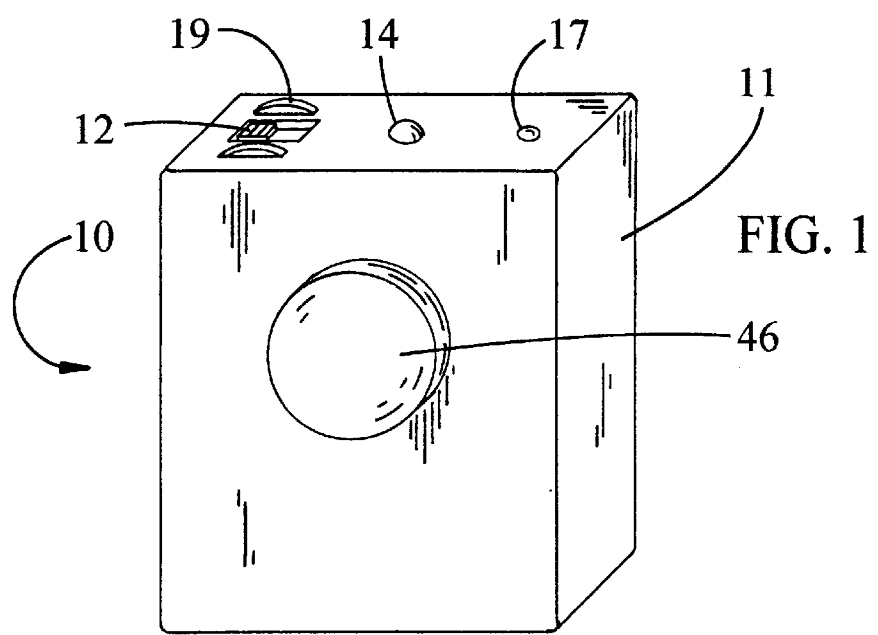
FIG. 1 is a perspective view of an apnea detector according to the present invention.
Figure 2:
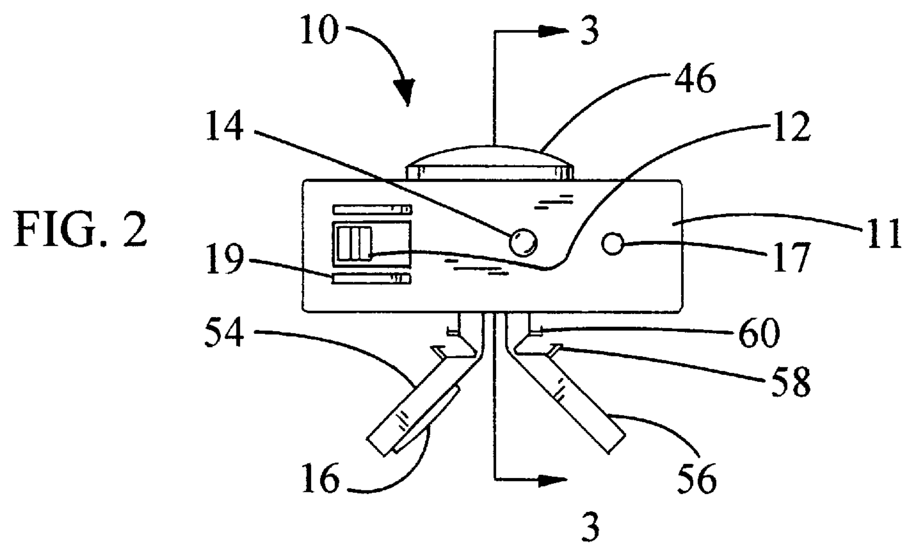
FIG. 2 is a top plan view of the apnea detector of FIG. 1.
Figure 3:
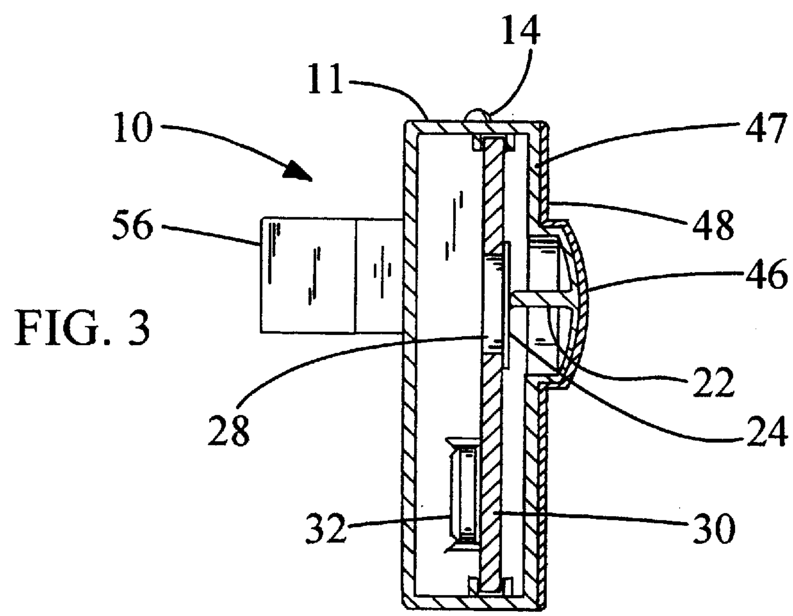
FIG. 3 is a cross section of the apnea detector taken along the line 3—3 in FIG. 2.
Figure 4:
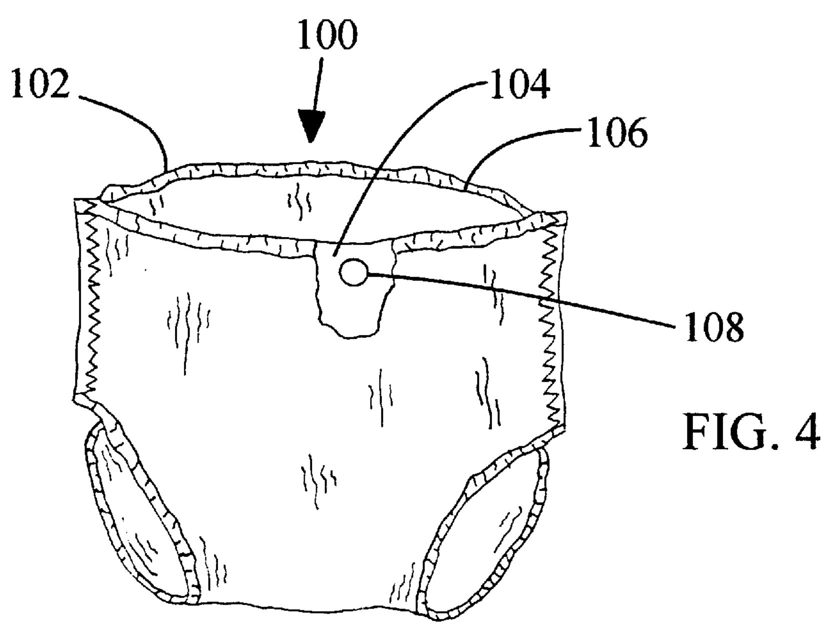
FIG. 4 is a perspective view of a partially sectioned, specially-designed article of clothing according to the present invention.
Figure 5:
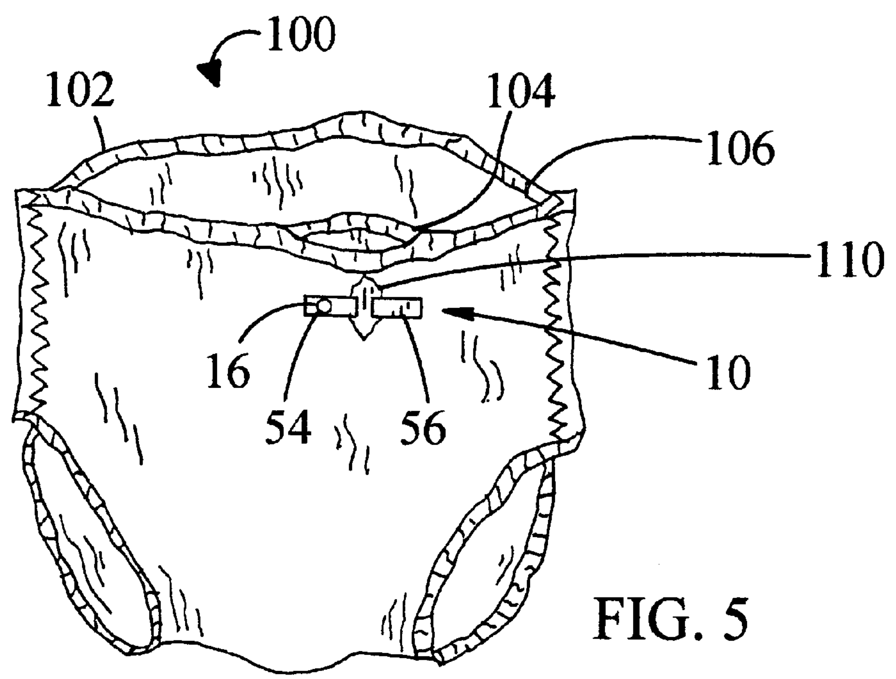
FIG. 5 is a perspective view of a complete apnea detecting system.

Looking more particularly to FIG. 1, a preferred embodiment of the present invention for an apnea detector is indicated generally at 10. FIG. 2 provides a top plan view of the apnea detector 10 while FIG. 3 is a cross section of the apnea detector 10 taken along the line 3—3 in FIG. 2. FIG. 4 depicts a piece of clothing, which in this case happens to comprise a diaper 100, that is specially designed for retaining the uniquely-structured apnea detector 10. Finally with respect to this first embodiment, FIG. 5 shows the apnea detector 10 installed relative to a specially designed diaper 100 whereby the diaper 100 and the apnea detector 10 together comprise an apnea detecting system 8.

As these figures show, the apnea detector 10 is founded on a body, which in this case comprises a shell 11. An ON/OFF switch 12 is disposed adjacent to a status LED 14. To prevent the ON/OFF switch 12 from being switched inadvertently, it is recessed and shielded by ridges 19. In practice, when the switch 12 is disposed in an ON position, the monitor LED 14, which is driven by a battery monitor circuit, will be lit to indicate that the apnea detector 10 is functioning properly with adequate power.

If the monitor LED 14 does not light up when the apnea detector 10 is switched ON, a user will be aware that the device is not functioning properly (e.g., it is without sufficient power). Alternatively or additionally and by means well known to one skilled in the art, the apnea detector 10 can further alert a user that the device is not functioning properly by the activation of a speaker 16, which is first shown in FIG. 2. With this, a user can be aware of a malfunction in the apnea detector 10 even when in another room or the like. To assuage the concerns of the user still further, a system test trigger 17 is included for manually triggering the speaker 16. With this, a user can depress the system test trigger 17 with, for example, a pencil tip for ensuring that the system is operating properly.

As FIG. 3 shows, a power source such as a battery 32 is operably associated with the apnea detector 10. In this case, the battery 32 is fixed to a printed circuit board 30. As one skilled in the art would expect, the printed circuit board 30 incorporates all necessary circuitry and components for performing the invention's timing, alarm, and other functions.

Looking to FIG. 2, one sees that first and second arms 54 and 56 are hingedly coupled to the main shell 11 of the apnea detector 10. Each of the first and second arms 54 and 56 is further provided with a means for locking the respective arm 54 or 56 in a position adjacent to the shell 11 of the apnea detector 10. Although the locking means certainly could assume many different forms, in this preferred embodiment the first and second arms 54 and 56 can be locked in place by a hook 58 that engages a ridge 60 when the first and second arms 54 and 56 are folded about their hinges 59. As will be explained in further detail below, the first and second arms 54 and 56 comprise a means for securing the apnea detector 10 to an article of clothing such as the diaper 100.

Figure 7:
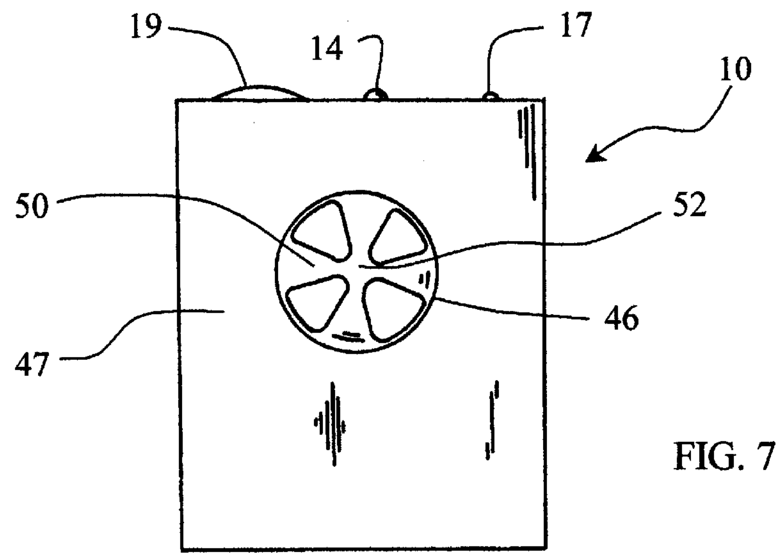
FIG. 7 is a view in front elevation of the apnea detector shown devoid of a protective layer.

Extending from the shell 11 is what may be termed a resilient dome 46, which forms a part of a means for sensing a respiratory movement of a subject. The resilient dome 46 is formed integrally with one wall 47 of the shell 11 of the apnea detector 10. Preferably, the wall 47 is formed from a durable, resilient material (i.e., plastic or the like) that will allow the resilient dome 46 to depress and return to its original configuration. As FIG. 3 shows, the entire wall 47 is shielded by a protective layer 48 of flexible, waterproof material, such as rubber. In FIG. 7, one sees the apnea detector 10 devoid of the protective layer 48. With this, it can be seen that the resilient dome 46 preferably comprises a hub 52 that is coupled to the wall 47 by a plurality of legs 50. As the figure shows, the wall 47, the legs 50, and the hub 52 are formed as a single piece in this preferred embodiment.

The resilient dome 46 cooperates with a plunger actuator 22 and a piezoelectric sheet 24 to act as a means for sensing a respiratory movement of a subject, which in this case comprises a means for inducing a mechanical movement in the apnea detector in response to a respiratory movement of a subject in combination with a means for converting the mechanical movement into an electrical signal. In doing so, the piezoelectric sheet 24 is fixed to a circuit board 30 bridging a displacement gap 28 that is formed in the circuit board 30. The plunger actuator 22 has a first end coupled to the resilient dome 46 and a second end disposed adjacent to the piezoelectric sheet 24. As a result, mechanical movement or deformation of the piezoelectric sheet 24 will be induced by a mechanical movement or displacement of the plunger actuator 22, which will be caused by a mechanical movement or depressing of the resilient dome 46. The depression of the resilient dome 46 will be induced by the respiratory movement of the subject's abdomen, which will result from the subject's breathing.

Figure 8:
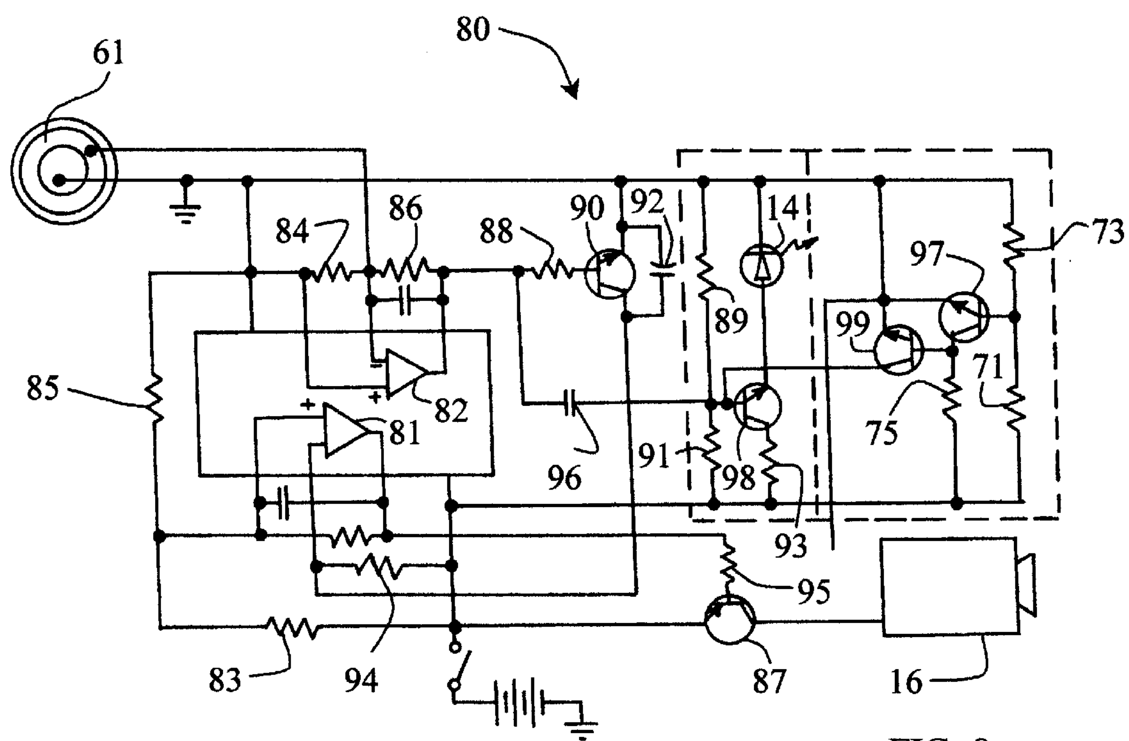
FIG. 8 is a schematic of an electronic circuit according to the present invention.

The resulting cyclic mechanical deformation of the piezoelectric sheet 24 forms an essential aspect of the electronic circuit of the present invention, which is indicated generally at 80 in FIG. 8. In the electronic circuit 80, a first op amp 82 has a positive input connected to ground and one side of the piezoelectric sheet 24 and a negative input connected to the second side of the piezoelectric sheet 24 with a transistor pair 84 and 86 setting the piezoelectric sheet's 24 gain. As the piezoelectric sheet 24 is deformed by the plunger actuator 22 in response to a respiratory movement of the subject's abdomen, op amp 82 produces a pulse which is applied through resistor 88 to transistor 90, which shunts capacitor 92. Capacitor 92 is part of an RC circuit including resistor 94, which has a predetermined time constant (i.e., thirty seconds). Alternatively, the invention can allow a manufacturer to adjust the time constant to accommodate the particular breathing characteristics and tendencies of a given subject. With this, respiratory movements of a subject will repeatedly reset the time delay unless a time period of greater than the time constant elapses without the occurrence of a respiratory movement.

A resistor bridge, indicated at 89 and 91, biases the transistor 98 just below its turn on point to adjust the sensitivity of transistor 98 to the pulse generated by op amp 82. Also, a resistor 93 limits the current through the LED 14. A second op amp 81 has a positive input that is biased to a set voltage by a pair of resistors 83 and 85. If the voltage across capacitor 92 charges above this set voltage, then the output of op amp 81 goes negative and is applied to the base of transistor 87 by resistor 95. This then turns the transistor 87 on thereby actuating a speaker 16 to provide an audible alarm indication that a time greater than the predetermined time constant has elapsed without the apnea detector's 10 detecting a respiratory movement of the subject.

Transistors 97 and 99 act as a low battery voltage indicator circuit. A pair of resistors 71 and 73 bias transistor 97 on until the battery's 32 voltage drops below a predetermined nominal voltage (i.e., eight volts). At that nominal voltage, the transistor 97 turns off and transistor 99 turns on with base current through resistor 75. With transistor 99 turned on, base current to transistor 98 is shunted therefrom thereby turning off transistor 98 and disabling LED 14 from being flashed. This non-flashing of the LED 14 will indicate to a user that the apnea detector 10 is without adequate power or is otherwise not operating properly. Conversely, when the LED 14 is flashing, a user can be confident that the apnea detector 10 is functioning properly with adequate power. Of course, and quite likely more preferably, a malfunction in the apnea detector 10 could be readily caused to trigger an audible alarm signal through the speaker 16 in addition or alternatively to the failure of the LED 14 to flash.

The inventor has realized that the safe and effective function of the apnea detector 10 practically demands that the resilient dome 46 be constantly and securely retained in direct contact with a subject's body. To see how the present invention accommodates this, one may look to FIG. 4 where an article of clothing, which in this case comprises a diaper 100, is shown devoid of an outer layer of a pocket 104. An aperture 108 is disposed in the upper portion of the front wall of the diaper 100 for receiving the resilient dome 46.

Advantageously, the pocket 104 and the shell 11 of the apnea detector 10 are correspondingly dimensioned such that, when the apnea detector 10 is disposed in the pocket 104 of the diaper 100, the aperture 108 aligns with the resilient dome 46 of the apnea detector 10. With this, the resilient dome 46 extends through the aperture 108, and direct contact is enjoyed between the resilient dome 46 and the subject's body while the apnea detector 10 is retained snugly in the pocket 104. Of course, the apnea detector 10, the resilient dome 46, the pocket 104, and the aperture 108 could be of a wide variety of shapes and sizes. It is necessary only that the overall configuration ensure that the resilient dome 46 align with the aperture 108 when the apnea detector 10 is disposed in the pocket 104. Furthermore, it should be clear that it is well within the scope of the present invention for the article of clothing to comprise any of a wide variety of types of clothing other than a diaper 100.

The diaper 100 of FIG. 4 is shown in complete form in FIG. 5 where one again sees that the diaper 100 has a pocket 104 interposed contiguously with the upper peripheral seam 106 of the elastic waistband 102 of the diaper 100 for receiving the apnea detector 10. With this, the apnea detector 10 essentially nests between the inner and outer layers of the diaper 100. The diaper 100 is shown to include further an aperture, which in this case comprises a slit 110, in the front wall thereof for receiving first and second legs 54 and 56 of the apnea detector 10 therethrough.

One will appreciate that the slit 110 could be cut into a standard diaper by a user seeking to install the apnea detector 10 therein. However, it would be most preferable to create the slit 110 during manufacture of the diaper 100 so it would be ensured that the slit 110 would be located and formed properly. For example, creating the slit 110 during manufacture would allow the slit 110 to have durable, sealed, and waterproof edges.

In use, the apnea detector 10 can be installed quickly and easily relative to a diaper 100 by a user who has substantially no experience or expertise. The apnea detector 10 need only be slipped into the pocket 104 with the resilient dome 46 oriented toward the subject's body and the first and second arms 54 and 56 facing away from the subject's body. With this, the distal ends of the first and second arms 54 and 56 can be passed through the slit 110, and then the first and second arms 54 and 56 can be locked in position adjacent to the shell 11 of the apnea detector 10 by folding the first and second arms 54 and 56 about their hinges 59 to engage the hooks 58 with the ridges 60. With this, the apnea detector 10 would be maintained in proper position most securely.

Of course, although it is not presently preferred, one should recognize that it is within the scope of the invention to associate the apnea detector 10 with a pocket 104 in a diaper 100 that does not have a slit 110. Accordingly, it will be equally clear that the apnea detector 10 could be installed without use of the first and second arms 54 and 56 or possibly devoid of the first and second arms 54 and 56 altogether.

Figure 6:
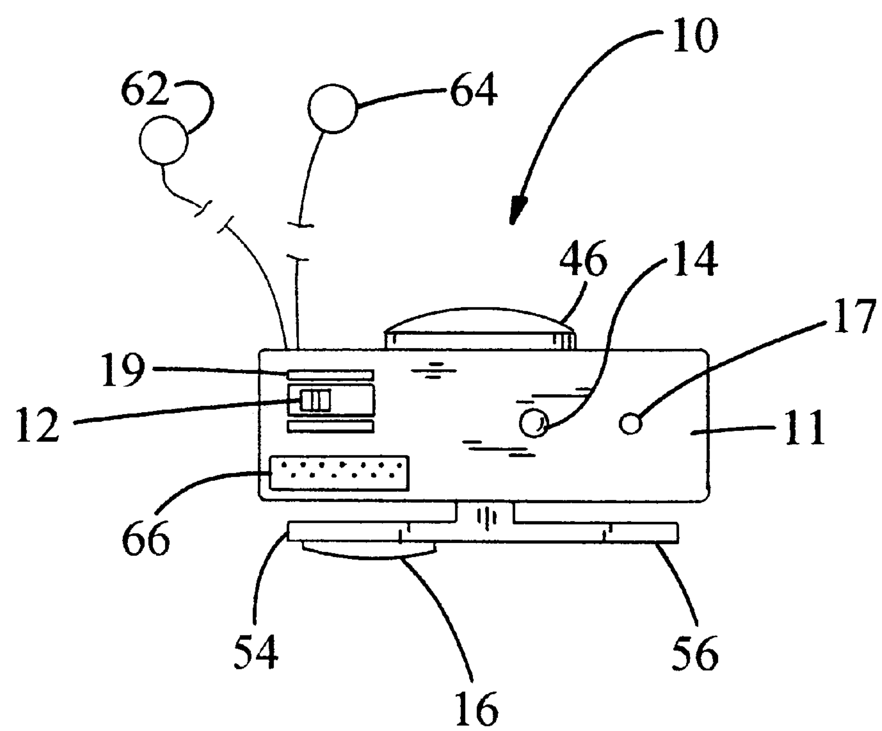
FIG. 6 is a top plan view of an alternative embodiment of the apnea detector.

FIG. 6 shows an alternative embodiment of the apnea detector 10 wherein the first and second arms 54 and 56 are fixed in a "T" orientation. Under this arrangement, the apnea detector 10 can be rotated relative to the slit 110 to align the first and second arms 54 and 56 with the slit 110 so that the first and second arms 54 and 56 can be passed through the slit 110. The apnea detector 10 could then be rotated relative to the slit 110 so that the first and second arms 54 and 56 are generally perpendicular to the slit 110 whereby the apnea detector 10 is locked in place. Of course, still further embodiments will be obvious in light of this disclosure.

As FIGS. 2, 5, and 6 show most clearly, the speaker 16 is advantageously disposed on the distal surface of the first leg 54 when the first leg 54 is locked in position adjacent to the shell 11 of the apnea detector 10. With this, the speaker 16 will be disposed adjacent to the exterior surface of the diaper 100 during use so that the speaker 16 will be readily audible when activated.

The embodiment of FIG. 6 is further improved by the provision of a heart monitor lead 62, a temperature sensor lead 64, and a data port 66. Certainly, the function of each of these is well known to one skilled in the art such that a detailed discussion of them will not be required to enable such a person to make and use this preferred embodiment of the invention. The heart monitor lead 62 and the temperature sensor lead 64 could monitor a wearer's heart rate and temperature respectively, and the circuit 80 could be provided with appropriate means for recording these statistics. The apnea detector 10 could be further adapted to trigger an alarm signal in response to an abnormality in either statistic. The apnea detector 10 could be further adapted to allow a user to download heart rate and temperature histories by means of appropriate circuitry and the data port 66. Although the heart monitor lead 62 and the temperature sensitive lead 64 are shown as elongate wire leads, it is well within the scope of the invention for them to be formed integrally with the main body of the apnea detector 10.

Figure 9:
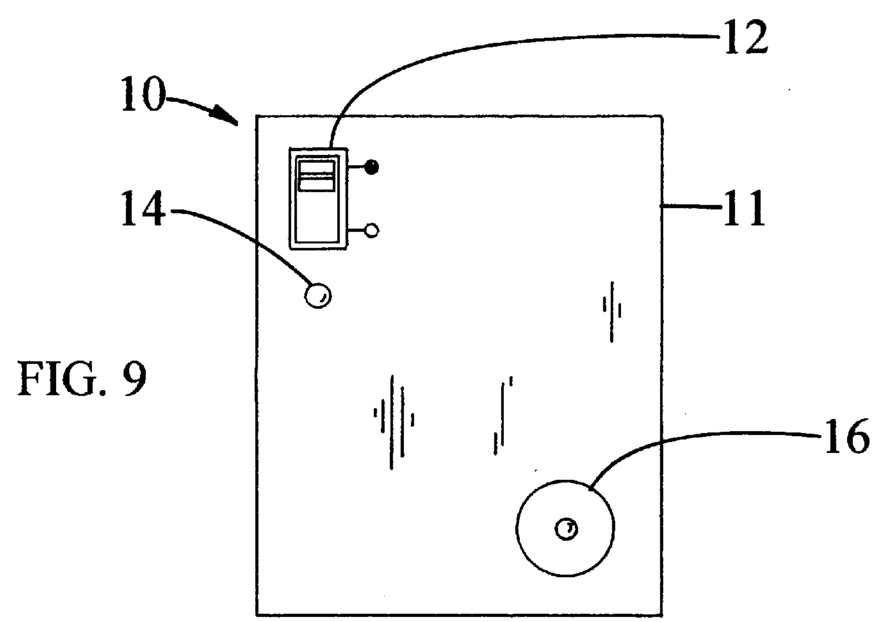
FIG. 9 is a view in front elevation of an alternative embodiment of the apnea detector.
Figure 10:
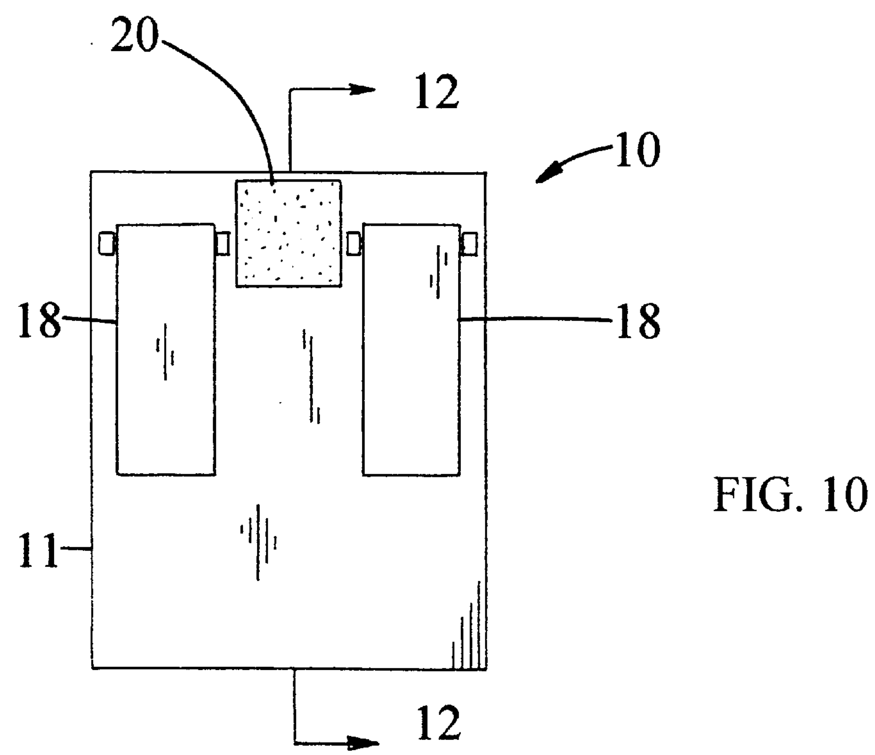
FIG. 10 is a view in rear elevation of the apnea detector of FIG. 9.
Figure 11:
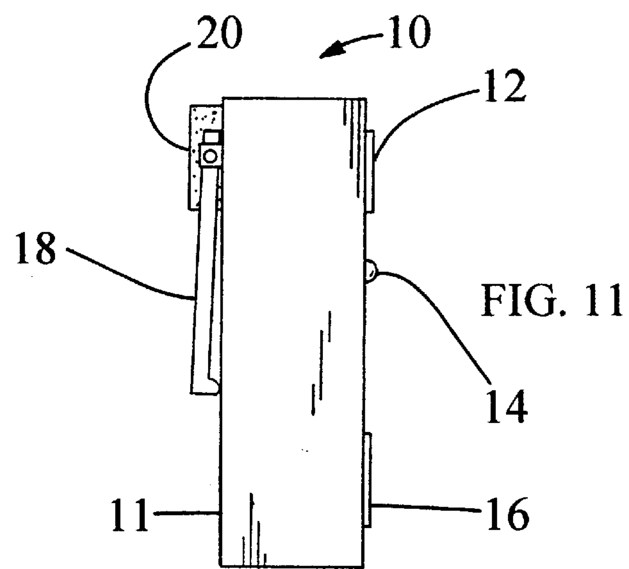
FIG. 11 is a view in side elevation of the apnea detector of FIG. 9.

FIGS. 9, 10, and 11 depict an alternatively preferred embodiment of the invention wherein the apnea detector 10 is not specifically designed for being retained in a pocket 104. To the contrary, in FIG. 10, one sees that the apnea detector 10 of this embodiment includes a means for coupling the device to a wearer's clothing. In this manifestation of the invention, the means for coupling the device to a wearer's clothing comprises clips 18. The apnea detector 10 further includes a rubber force-receiving pad 20, which is intended to be operationally equivalent to the resilient dome 46 of the previous embodiment.

Figure 12:
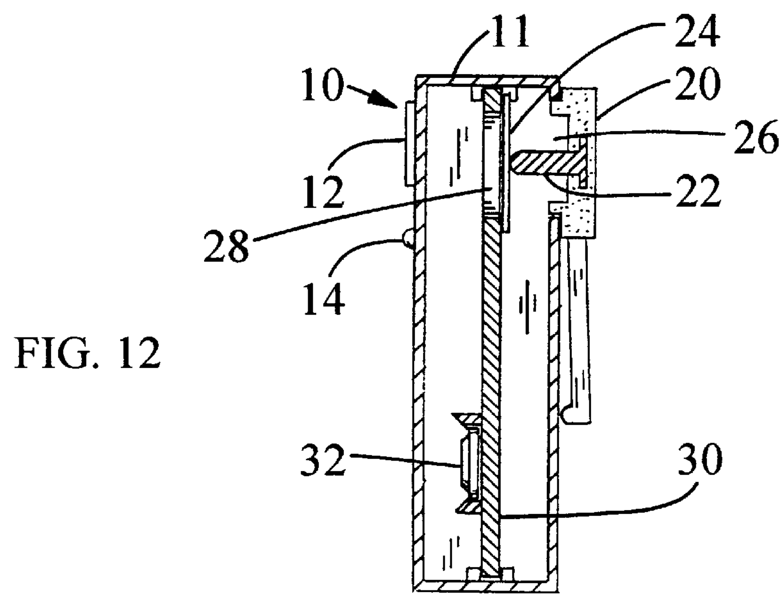
FIG. 12 is a is a cross section of the apnea detector taken along the line 12—12 in FIG. 10.

FIG. 12 is a cross-sectional view of the apnea detector 10 taken along the line 12—12 in FIG. 10. The means for sensing a respiratory movement of a subject comprises the rubber force receiving pad 20, a plunger actuator 22, and a piezoelectric sheet 24. This sensing means again may be considered a means for inducing a mechanical movement in the apnea detector in response to a respiratory movement of a subject in combination with a means for converting the mechanical movement into an electrical signal. In this embodiment of the invention, the rubber force-receiving pad 20 bridges a displacement gap 26 in the shell 11 of the apnea detector 10. The plunger actuator 22 has a first end embedded in the rubber force receiving pad 20 and a second end disposed adjacent to the piezoelectric sheet 24. The piezoelectric sheet 24 again bridges a displacement gap 28 in a printed circuit board 30.

Figure 13:
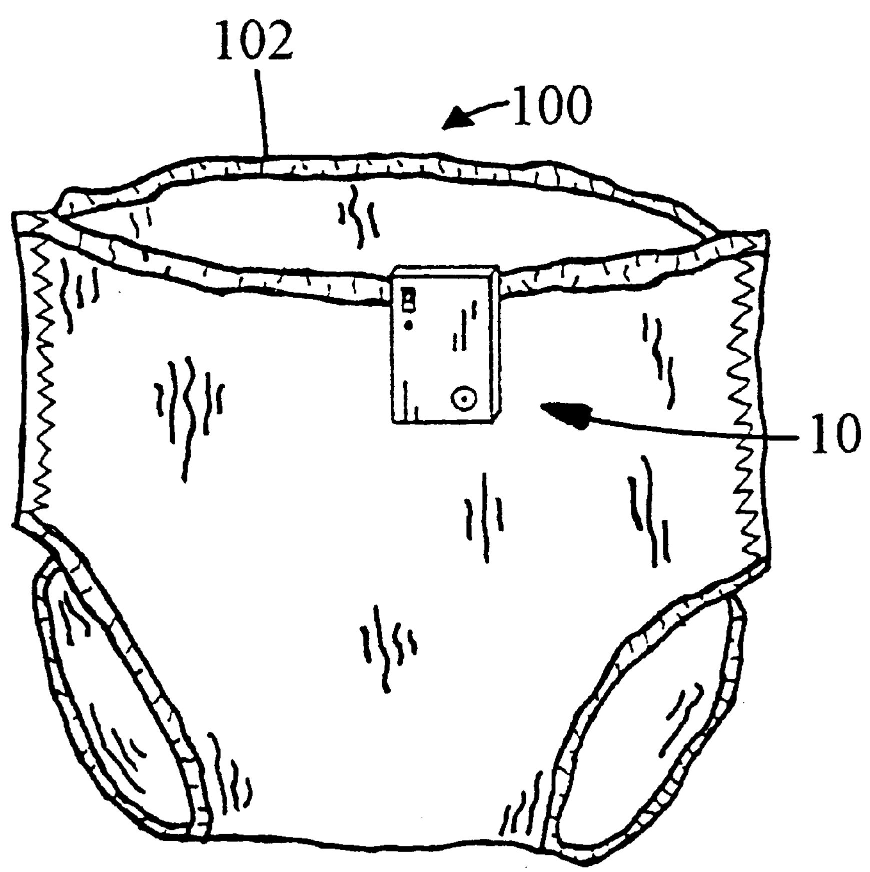
FIG. 13 is a perspective view of the alternative embodiment of the apnea detecting system.

FIG. 13 is a perspective view of an apnea detector 10 according to the present invention shown coupled to a diaper 100, which probably would be the most advantageous place to couple the device when it is employed to monitor the respiration of a very young child. As one can see, the apnea detector 10 is clipped over the elastic waistband 102 of the diaper 100 by use of the clips 18. The diaper 100 may be of the typical disposable type. As FIG. 13 indicates, it is presently contemplated that the apnea detector 10 would be located most advantageously on the diaper 100 adjacent to a subject's abdomen.

Figure 14:
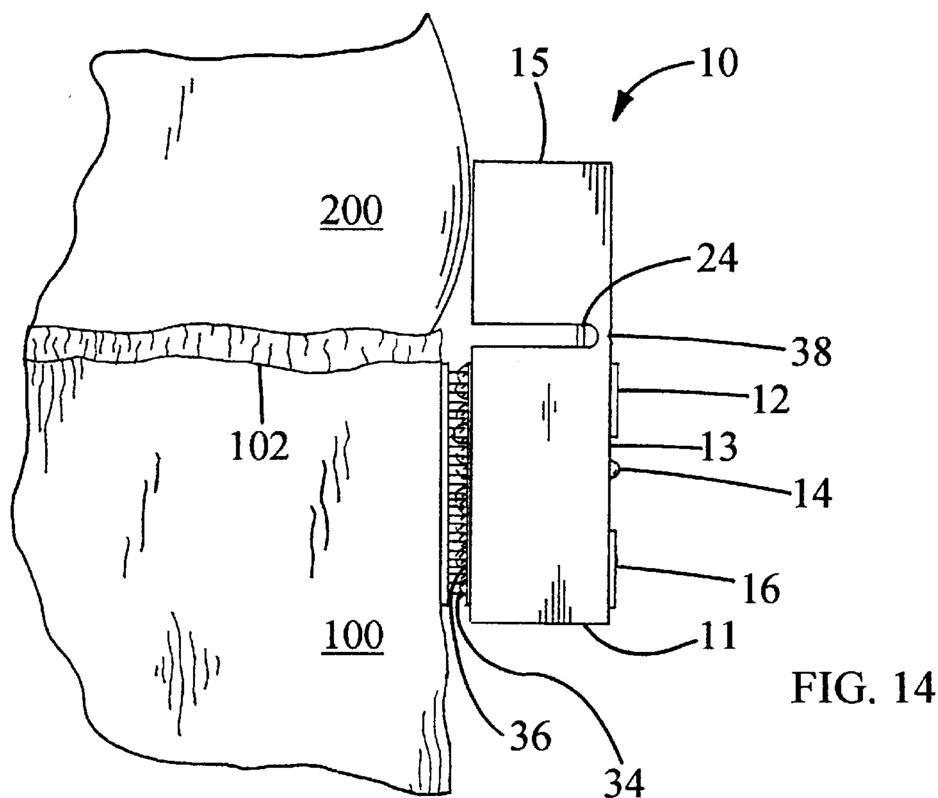
FIG. 14 is a view in side elevation of another alternative embodiment of the invention shown coupled to a subject's body.

FIG. 14 depicts another embodiment of the invention for an apnea detector 10 again shown coupled to a diaper 100, which is disposed on a subject's body 200. In this embodiment, the means for coupling the apnea detector 10 to a subject's diaper 100 comprises a hook and loop combination wherein an area of hook material 34 is disposed on the apnea detector 10 while an area of loop material 36 is disposed on the diaper 100. With this, the apnea detector 10 can be removably attached to the diaper 100 in a most simple and comfortable manner.

FIG. 14 also shows that in this embodiment of the apnea detector 10 the shell 11 comprises a first section 13 that is coupled to a second section 15 along a living hinge 38 that may be formed of flexible plastic or the like. A piezoelectric sheet 24 bridges a gap between the first and second sections 13 and 15 of the shell 11 at a position slightly displaced from the living hinge 38. The apnea detector 10 is coupled to the diaper 100 with the second section 15 of the shell 11 disposed in contact with the subject's body 200 (i.e., the subject's abdomen). In operation, when the subject breathes, the subject's abdomen will exhibit a respiratory movement that will induce a pivoting of the second section 15 relative to the first section 13 about the living hinge 38. This pivoting in turn will induce a strain to the piezoelectric sheet 24, which will convert this mechanical movement to an electrical impulse signal. With this, one sees that the hinged coupling of the first and second sections 13 and 15 and the piezoelectric sheet 24 act as the invention's means for inducing a mechanical movement in the apnea detector in response to a respiratory movement of a subject and the means for converting the mechanical movement into an electrical signal. The resulting electrical impulse signal will allow function of the apnea detector 10 in much the same manner as was previously described.

Figure 15:
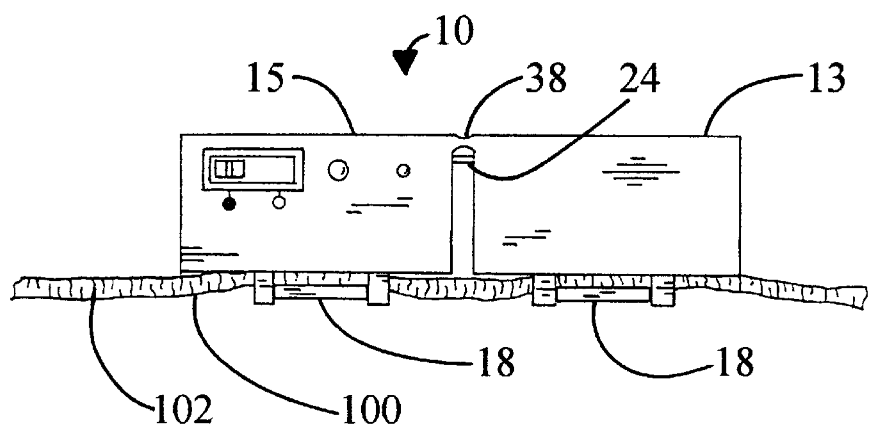
FIG. 15 is a top plan view of still another embodiment of the invention.

FIG. 15 shows still another embodiment of the present invention for an apnea detector 10. In FIG. 15, the apnea detector 10 is similar in operation to that shown in FIG. 14 in that the piezoelectric sheet 24 is disposed slightly displaced from the living hinge 38 whereby a respiratory movement produces an electrical impulse signal. However, in this embodiment the first and second sections 13 and 15 are disposed in a side-by-side relationship as opposed to the top-and-bottom relationship depicted in FIG. 15. The apnea detector 10 of FIG. 15 is different than the embodiment of FIG. 14 for the further reason that it is coupled to the elastic waistband 102 of a subject's diaper 100 by a clip 18 disposed on each of the first and second sections 13 and 15.

In light of the foregoing, it will be apparent that the present invention provides a number of advantages over prior art apnea detectors. Most importantly, the apnea detecting system 8 securely retains the apnea detector 10 such that it always functions effectively thereby ensuring that any cessation in a wearer's breathing will be detected and an alarm signal will be actuated in response thereto. Advantageously, the apnea detector 10 is so retained without presenting discomfort to a wearer. Furthermore, by maintaining its position without need for a strap or a belt, the apnea detector 10 effectively can not act as an independent source of danger to a child who wears it. Even further still, the apnea detector 10 can be installed relative to an article of clothing, such as the diaper 100, with great ease and little opportunity for mistake by a user who needs substantially no expertise. Of course, further advantages of the present invention will be readily obvious both to one who has reviewed the present disclosure and to one who has an opportunity to make use of an embodiment of the present invention.

It will be clear that the present invention has been shown and described with reference to certain preferred embodiments that merely exemplify the broader invention revealed herein. Certainly, those skilled in the art can conceive of alternative embodiments. For instance, those with the major features of the invention in mind could craft embodiments that incorporate those major features while not incorporating all of the features included in the preferred embodiments. With the foregoing in mind, the following claims are intended to define the scope of protection to be afforded the inventor, and the claims shall be deemed to include equivalent constructions insofar as they do not depart from the spirit and scope of the present invention.

One must note that a plurality of the following claims express certain elements as a means for performing a specific function, at times without the recital of structure or material. As the law demands, these claims shall be construed to cover not only the corresponding structure and material expressly described in this specification but also equivalents thereof.

I claim as deserving the protection of United States Letters Patent:

1. An apnea detecting system for monitoring a cyclic respiratory movement of a subject's body and for triggering an alarm signal in response to a cessation in that respiratory movement, the apnea detecting system comprising an article of clothing for retaining an apnea detector that has a projection from an apnea detector body for sensing a respiratory movement of a subject, the article of clothing comprising:

- a body covering element for covering a portion of a subject's body;
- an aperture in the body covering element for aligning with the projection from the body of an apnea detector; and
- a means for retaining an apnea detector relative to the article of clothing with the projection from the body of the apnea detector aligned with the aperture in the body covering element of the article of clothing;

whereby the article of clothing is capable of retaining an apnea detector for consistently effective function of the apnea detector with the projection from the apnea detector projecting into the aperture in the article of clothing.

2. The apnea detecting system of claim 1 wherein the means for retaining an apnea detector relative to the article of clothing with the projection from the body of the apnea detector aligned with the aperture in the body covering element of the article of clothing comprises a pocket disposed on the body covering element wherein the pocket is defined by an inside wall for being disposed proximal to a subject's body and an outside wall for being disposed distal to a subject's body and wherein the aperture in the body covering element is disposed in the inside wall of the pocket for aligning with the projection from the body of an apnea detector whereby an apnea detector can be retained securely in the pocket of the article of clothing without the apnea detector posing a risk of discomfort or danger to the subject.

3. The apnea detecting system of claim 2 wherein the article of clothing comprises a diaper.

4. The apnea detecting system of claim 2 wherein the article of clothing further comprises an aperture in the outside wall of the pocket for receiving a means for securing an apnea detector within the pocket of the article of clothing.

5. The apnea detecting system of claim 1 wherein the aperture in the body covering element of the article of clothing comprises an annular opening.

6. The apnea detecting system of claim 4 wherein the aperture in the outside wall of the pocket of the article of clothing comprises a slit and wherein the aperture in the inside wall of the pocket of the article of clothing comprises an annular opening.

7. The apnea detecting system of claim 1 further comprising an apnea detector for monitoring a cyclic respiratory movement of a subject's body and for triggering an alarm signal in response to a cessation in that respiratory movement wherein the apnea detector comprises a body for being retained adjacent to a subject's body by the means for retaining an apnea detector relative to the article of clothing wherein the body of the apnea detector has a first side and a second side and a means for sensing a respiratory movement of a subject comprising a projection disposed on the first side of the body of the apnea detector wherein the projection from the body of the apnea detector and the aperture in the article of clothing are disposed to align when the apnea detector is retained relative to the article of clothing.

8. The apnea detecting system of claim 7 wherein the means for retaining an apnea detector relative to the article of clothing with the projection from the body of the apnea detector aligned with the aperture in the body covering element of the article of clothing comprises a pocket disposed on the body covering element wherein the pocket is defined by an inside wall for being disposed proximal to a subject's body and an outside wall for being disposed distal to a subject's body and wherein the aperture in the body covering element is disposed in the inside wall of the pocket for aligning with the projection from the body of the apnea detector whereby the apnea detector can be retained securely in the pocket of the article of clothing without the apnea detector posing a risk of discomfort or danger to the subject.

9. The apnea detecting system of claim 8 wherein the article of clothing further comprises a second aperture in the pocket and wherein the apnea detector further comprises at least a first leg that projects from the apnea detector for engaging the second aperture of the pocket whereby the second aperture of the pocket and the at least one leg that projects from the apnea detector together comprise a means for securing the apnea detector within the pocket of the article of clothing.

10. The apnea detecting system of claim 9 wherein the second aperture in the pocket of the article of clothing comprises a slit and wherein the aperture in the inside wall of the pocket of the article of clothing comprises an annular opening.

11. The apnea detecting system of claim 9 further comprising a second leg that projects from the apnea detector for additionally engaging the second aperture in the pocket of the article of clothing.

12. The apnea detecting system of claim 11 wherein the first and second legs are fixed in position with a proximal side of each leg facing the body of the apnea detector and a distal side of each leg facing away from the body of the apnea detector.

13. The apnea detecting system of claim 11 wherein the first and second legs each are hingedly coupled to the body of the apnea detector and further comprising a means for locking the first and second legs in position with a proximal side of each leg facing the body of the apnea detector and a distal side of each leg facing away from the body of the apnea detector.

14. The apnea detecting system of claim 9 wherein the second aperture is disposed in the outside wall of the pocket and further comprising a means for providing an alarm signal disposed on the first leg whereby the means for providing an alarm signal will be disposed exterior to the outside wall of the pocket when the apnea detector is disposed within the pocket of the article of clothing with the first leg in engagement with the second aperture in the pocket.

15. An apnea detecting system for monitoring a cyclic respiratory movement of a subject's body and for triggering an alarm signal in response to an abnormality in that respiratory movement, the apnea detecting system comprising an apnea detector that comprises:

an apnea detector body for being retained adjacent to a subject's body;

a means operably associated with the apnea detector body for sensing a respiratory movement of a subject;

a means operably associated with the apnea detector body for triggering an alarm signal in response to an abnormality in the respiratory movement of a subject;

a means operably associated with the apnea detector body for providing an alarm signal in response to an activation by the alarm triggering means;

at least a first leg that projects from the apnea detector for securing the apnea detector in place relative to an article of clothing wherein the first leg comprises a clip for clipping the apnea detector to an article of clothing.

16. The apnea detecting system of claim 15 wherein the means for sensing a respiratory movement of a subject comprises a resilient projection disposed on a first side of the body of the apnea detector for mechanically moving cyclically in response to a cyclic respiratory movement of a subject.

17. The apnea detecting system of claim 16 wherein the resilient projection is formed integrally as a single member with a wall of the body of the apnea detector and wherein the resilient projection comprises a hub coupled to the wall by a plurality of legs.

18. The apnea detecting system of claim 16 wherein the means for sensing a respiratory movement of a subject further comprises a means for converting a mechanical movement of the resilient projection into an electric signal.

19. The apnea detecting system of claim 18 wherein the means for converting a mechanical movement of the resilient projection into an electric signal comprises a piezoelectric member wherein a mechanical movement of the resilient projection induces a deformation in the piezoelectric member with a consequent generation of an electric signal.

20. The apnea detecting system of claim 15 further comprising a second leg that projects from the apnea detector for further securing the apnea detector in place relative to an article of clothing wherein the second leg comprises a clip for clipping the apnea detector to an article of clothing.

21. The apnea detecting system of claim 20 wherein the first and second legs are pivotably coupled to the body of the apnea detector with a proximal side of each leg facing the body of the apnea detector and a distal side of each leg facing away from the body of the apnea detector.

22. The apnea detecting system of claim 21 wherein the first and second legs each are hingedly coupled to the body of the apnea detector.

23. An apnea detecting system for monitoring a cyclic respiratory movement of a subject's body and for triggering an alarm signal in response to an abnormality in that respiratory movement, the apnea detecting system comprising an apnea detector and an article of clothing wherein the apnea detector comprises:

an apnea detector body for being retained adjacent to a subject's body;

a resilient projection disposed on a first side of the body of the apnea detector for mechanically moving cyclically in response to a cyclic respiratory movement of a subject;

a means for converting a mechanical movement of the resilient projection into an electric signal;

a means operably associated with the apnea detector body for triggering an alarm signal in response to an abnormality in the respiratory movement of a subject; and a means operably associated with the apnea detector body for providing an alarm signal in response to an activation by the alarm triggering means;

wherein the article of clothing comprises:

a body covering element for covering a portion of a subject's body;

an aperture in the body covering element for aligning with the resilient projection from the apnea detector body; and a means for retaining an apnea detector relative to the article of clothing with the projection from the body of the apnea detector aligned with the aperture in the body covering element of the article of clothing;

whereby the article of clothing is capable of retaining the apnea detector for consistently effective function of the apnea detector with the projection from the apnea detector projecting into the aperture in the article of clothing.

24. The apnea detecting system of claim 23 wherein the means for retaining the apnea detector relative to the article of clothing with the projection from the body of the apnea detector aligned with the aperture in the body covering element of the article of clothing comprises a pocket disposed on the body covering element wherein the pocket is defined by an inside wall for being disposed proximal to a subject's body and an outside wall for being disposed distal to a subject's body and wherein the aperture in the body covering element is disposed in the inside wall of the pocket for aligning with the projection from the apnea detector body whereby the apnea detector can be retained securely in the pocket of the article of clothing without the apnea detector posing a risk of discomfort or danger to the subject.

25. The apnea detecting system of claim 24 wherein the article of clothing further comprises a second aperture in the pocket and wherein the apnea detector further comprises at least a first leg that projects from the apnea detector for engaging the second aperture in the pocket thereby further securing the apnea detector within the pocket of the article of clothing.

26. The apnea detecting system of claim 25 wherein the first leg is fixed in position with a proximal side of the first leg facing the body of the apnea detector and a distal side of the first leg facing away from the body of the apnea detector.

27. The apnea detecting system of claim 25 wherein the first leg is hingedly coupled to the body of the apnea detector and further comprising a means for locking the first leg in position with a proximal side of the first leg facing the body of the apnea detector and a distal side of the first leg facing away from the body of the apnea detector.

28. The apnea detecting system of claim 25 wherein the second aperture is disposed in the outside wall of the pocket and further comprising a means for providing an alarm signal disposed on the first leg whereby the means for providing an alarm signal will be disposed exterior to the outside wall of the pocket when the apnea detector is disposed within the pocket of the article of clothing with the first leg in engagement with the aperture in the outside wall of the pocket.

29. An apnea detecting system for monitoring a cyclic respiratory movement of a subject's body and for triggering an alarm signal in response to an abnormality in that respiratory movement, the apnea detecting system comprising an apnea detector that comprises:

an apnea detector body for being retained adjacent to a subject's body wherein the apnea detector body comprises a first section and a second section wherein the first section is coupled to the second section by a hinge member;

a means operably associated with the apnea detector body for sensing a respiratory movement of a subject wherein the means for sensing a respiratory movement of a subject comprises a means for converting a mechanical movement of the first section relative to the second section into an electrical signal;

a means operably associated with the apnea detector body for triggering an alarm signal in response to an abnormality in the respiratory movement of a subject; and a means operably associated with the apnea detector body for providing an alarm signal in response to an activation by the alarm triggering means.

30. The apnea detecting system of claim 29 wherein the means for converting a mechanical movement of the first section relative to the second section comprises a piezoelectric member coupled at a first location to the first section of the apnea detector body and coupled at a second location to the second section of the apnea detector body whereby the piezoelectric member bridges between the first and second sections of the apnea detector body and a pivoting of the first section of the apnea detector body relative to the second section of the apnea detector body will tend to cause mechanical strain in the piezoelectric member.

31. An apnea detecting system for monitoring a cyclic respiratory movement of a subject's body and for triggering an alarm signal in response to an abnormality in that respiratory movement, the apnea detecting system comprising an apnea detector that comprises:

an apnea detector body for being retained adjacent to a subject's body;

a means operably associated with the apnea detector body for sensing a respiratory movement of a subject;

a means operably associated with the apnea detector body for triggering an alarm signal in response to an abnormality in the respiratory movement of a subject;

a means operably associated with the apnea detector body for providing an alarm signal in response to an activation by the alarm triggering means; and a means for monitoring a subject's temperature.

32. An apnea detecting system for monitoring a cyclic respiratory movement of a subject's body and for triggering an alarm signal in response to an abnormality in that respiratory movement, the apnea detecting system comprising an apnea detector that comprises:

an apnea detector body for being retained adjacent to a subject's body;

a means operably associated with the apnea detector body for sensing a respiratory movement of a subject;

a means operably associated with the apnea detector body for triggering an alarm signal in response to an abnormality in the respiratory movement of a subject;

a means operably associated with the apnea detector body for providing an alarm signal in response to an activation by the alarm triggering means; and a means for monitoring a subject's heart beat.

33. An apnea detecting system for monitoring a cyclic respiratory movement of a subject's body and for triggering an alarm signal in response to an abnormality in that respiratory movement, the apnea detecting system comprising an apnea detector that comprises:

an apnea detector body for being retained adjacent to a subject's body;

a means operably associated with the apnea detector body for sensing a respiratory movement of a subject;

a means operably associated with the apnea detector body for triggering an alarm signal in response to an abnormality in the respiratory movement of a subject;

a means operably associated with the apnea detector body for providing an alarm signal in response to an activation by the alarm triggering means; and a means for selectively adjusting a time constant beyond which an alarm signal will be triggered by the means operably associated with the apnea detector body for triggering an alarm signal in response to an abnormality in the respiratory movement of a subject.

* * * * *